(12) United States Patent
Alarcon Heredia et al.

(10) Patent No.: US 9,823,163 B2
(45) Date of Patent: Nov. 21, 2017

(54) APPARATUS, SYSTEMS AND METHODS FOR IMPROVING VISUAL OUTCOMES FOR PSEUDOPHAKIC PATIENTS

(71) Applicant: AMO Groningen B.V., Groningen (NL)

(72) Inventors: Aixa Alarcon Heredia, Groningen (NL); Carmen Canovas Vidal, Groningen (NL); Robert Rosén, Groningen (NL); Hendrik A. Weeber, Groningen (NL); Patricia Ann Piers, Groningen (NL)

(73) Assignee: AMO GRONINGEN B.V., Groningen (NL)

( * ) Notice: Subject to any disclaimer, the term of this patent is extended or adjusted under 35 U.S.C. 154(b) by 0 days.

(21) Appl. No.: 14/878,294

(22) Filed: Oct. 8, 2015

(65) Prior Publication Data

US 2016/0161364 A1     Jun. 9, 2016

Related U.S. Application Data

(60) Provisional application No. 62/087,585, filed on Dec. 4, 2014.

(51) Int. Cl.
*G01B 9/00* (2006.01)
*G01M 11/02* (2006.01)
*G06F 19/00* (2011.01)

(52) U.S. Cl.
CPC .... *G01M 11/0292* (2013.01); *G01M 11/0235* (2013.01); *G06F 19/3437* (2013.01)

(58) Field of Classification Search
CPC ............. G01M 11/0292; G01M 11/00; G01M 11/0264; G01M 11/0242; G01M 11/0221

USPC ...................................................... 356/124.5
See application file for complete search history.

(56) References Cited

U.S. PATENT DOCUMENTS

| 2002/0071097 | A1* | 6/2002 | Ross, III | A61B 3/1015 351/212 |
| 2010/0134760 | A1* | 6/2010 | Salvati | A61B 3/0025 351/206 |
| 2011/0270596 | A1 | 11/2011 | Weeber | |
| 2012/0296422 | A1* | 11/2012 | Weeber | A61F 2/1637 623/6.11 |

(Continued)

FOREIGN PATENT DOCUMENTS

| WO | 0234126 A1 | 5/2002 |
| WO | 2012024152 A1 | 2/2012 |

OTHER PUBLICATIONS

International Search Report and Written Opinion for Application No. PCT/IB2015/002109, dated Mar. 15, 2016, 11 pages.

*Primary Examiner* — Tarifur Chowdhury
*Assistant Examiner* — Md M Rahman
(74) *Attorney, Agent, or Firm* — Abbott Medical Optics Inc.

(57) ABSTRACT

A system and method of characterizing through-focus visual performance of an IOL using metrics based on an area under the modulation transfer function for different spatial frequencies at different defocus positions of the IOL. Also disclosed is a system and method of characterizing through-focus visual performance of an IOL using a metric based on an area under a cross-correlation coefficient for an image of a target acquired by the IOL at different defocus positions of the IOL.

12 Claims, 12 Drawing Sheets

(56) References Cited

U.S. PATENT DOCUMENTS

2012/0310133 A1* 12/2012 De Juan, Jr. .......... A61F 9/0017
602/43
2013/0286351 A1* 10/2013 Shimizu ................. A61B 3/107
351/212

* cited by examiner

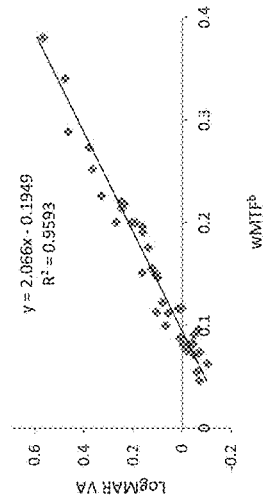
Figure 1A. MTFa
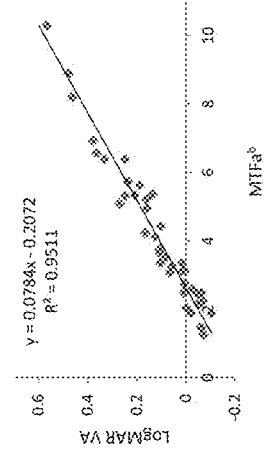
Figure 1B. wMTF
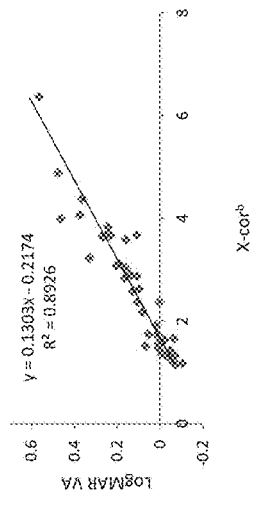
Figure 1C. wOTF
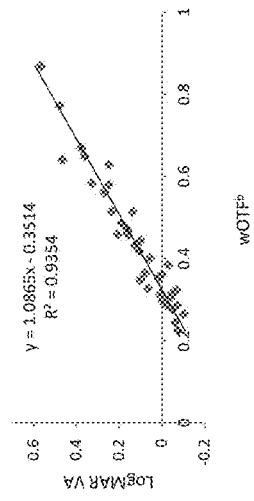
Figure 1D. X-cor

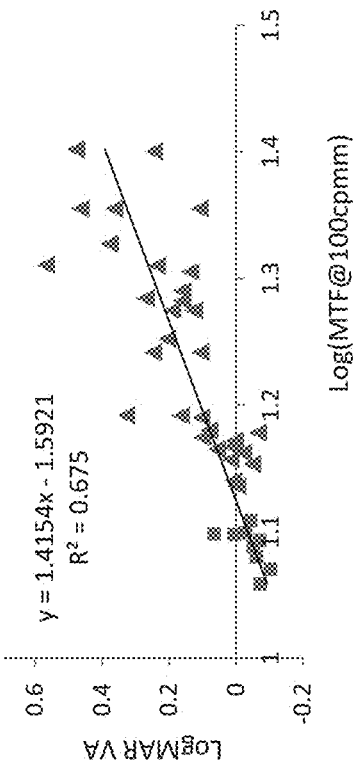
Figure 3A. MTF at 50c/mm
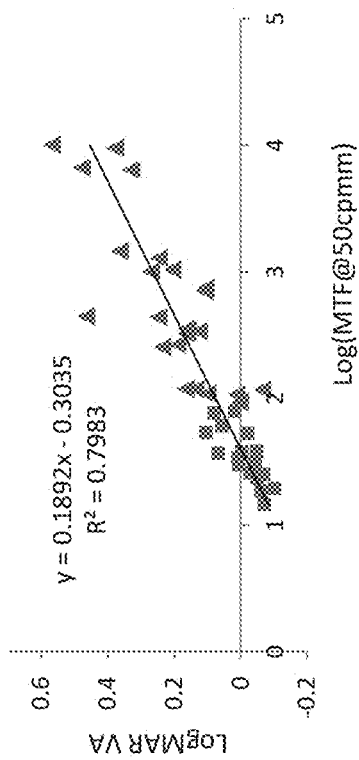
Figure 3B. MTF at 100c/mm

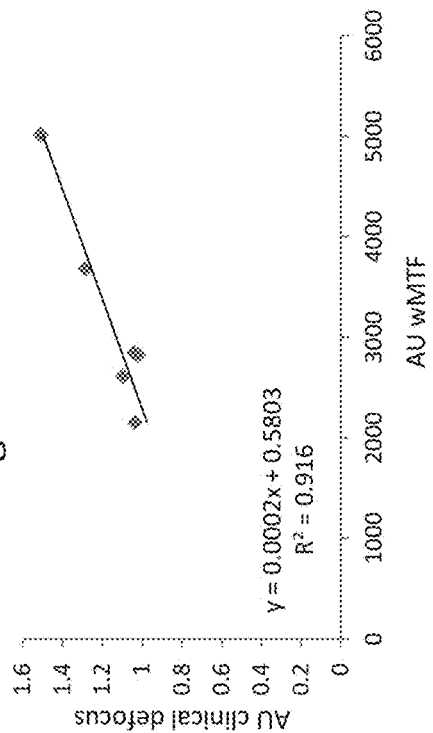
Figure 4A. MTFa
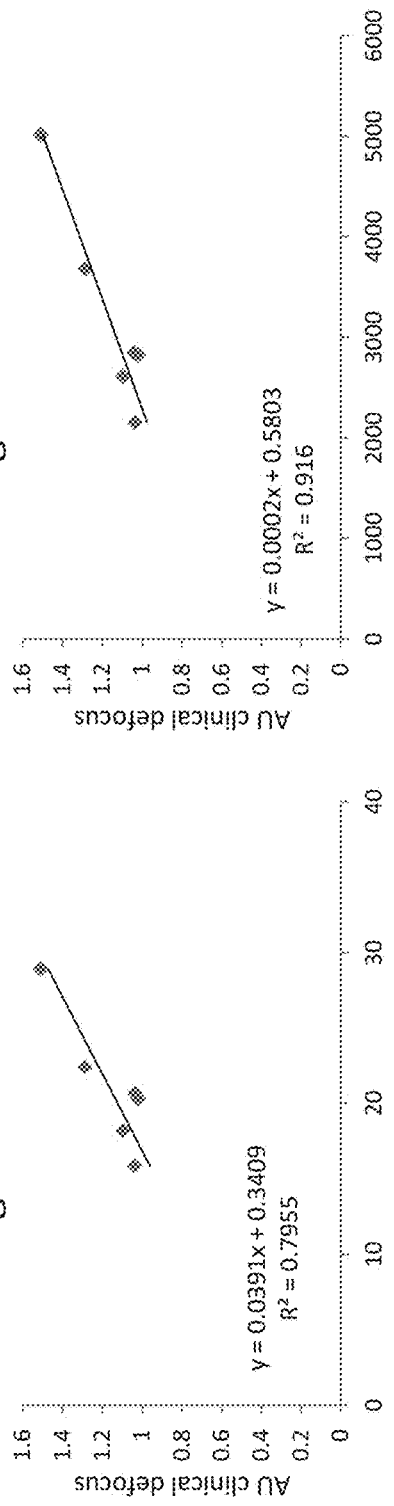
Figure 4B. wMTF
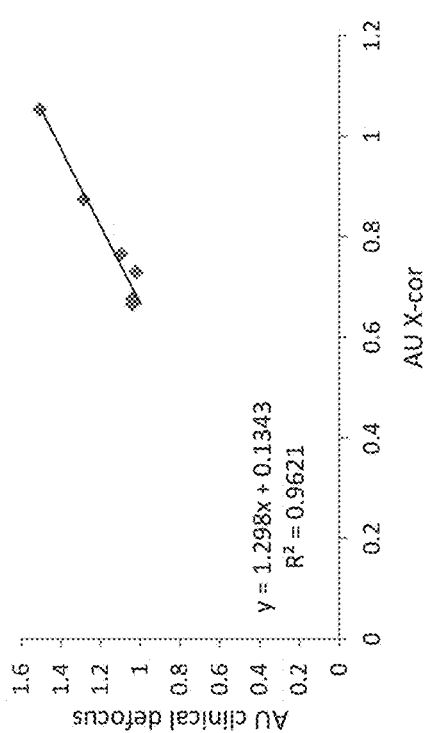
Figure 4C. wOTF
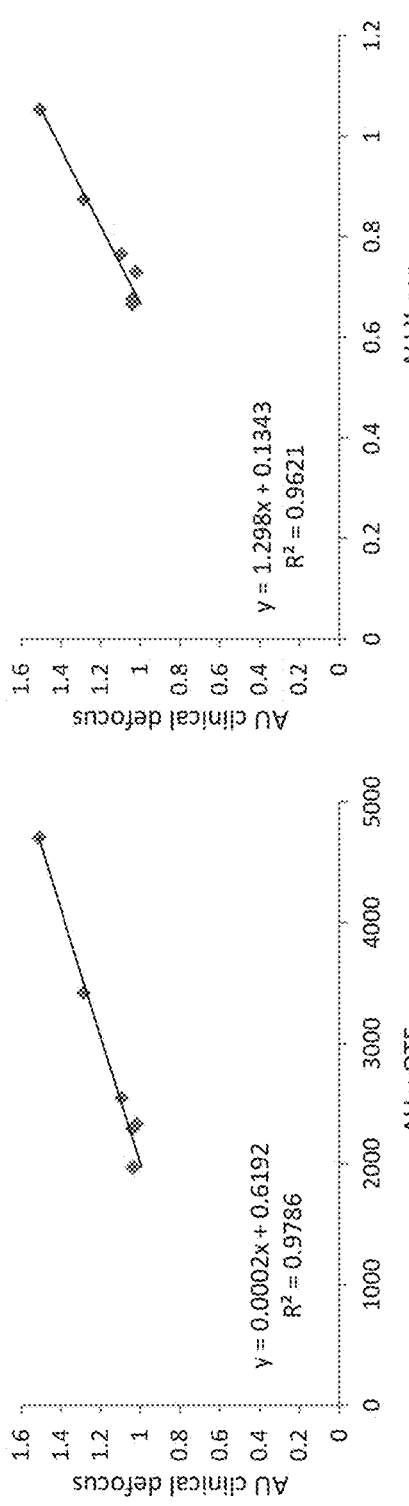
Figure 4D. X-cor

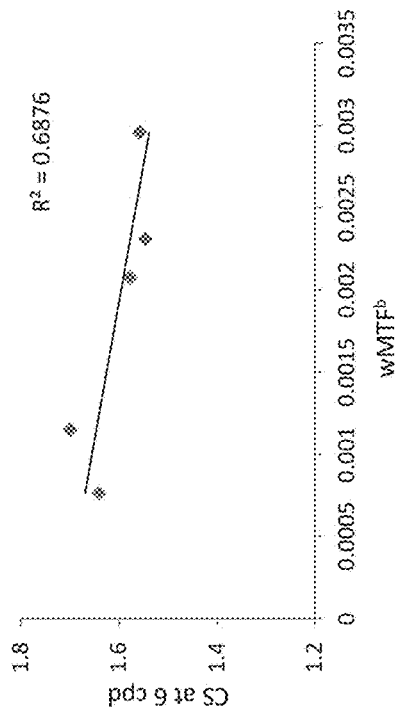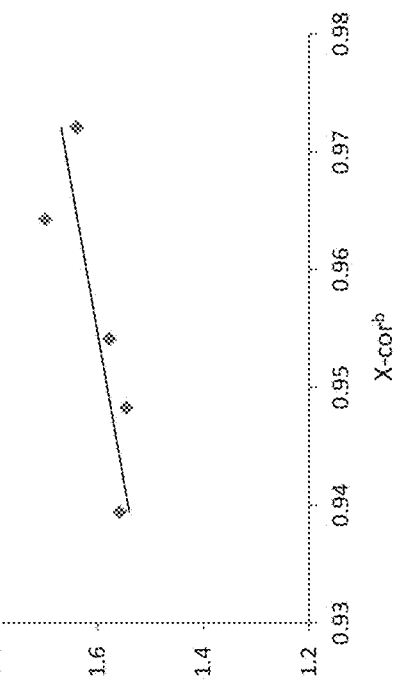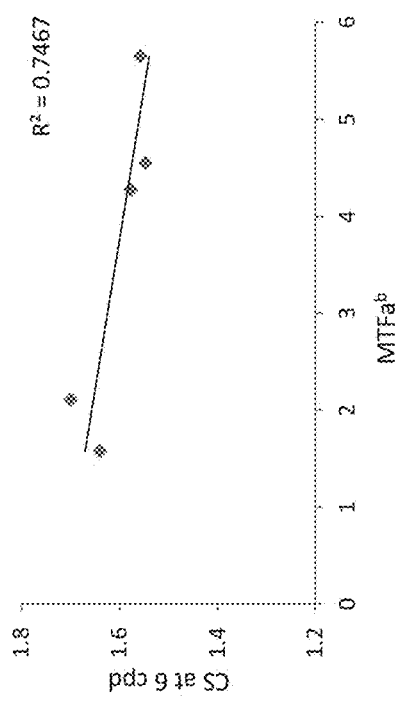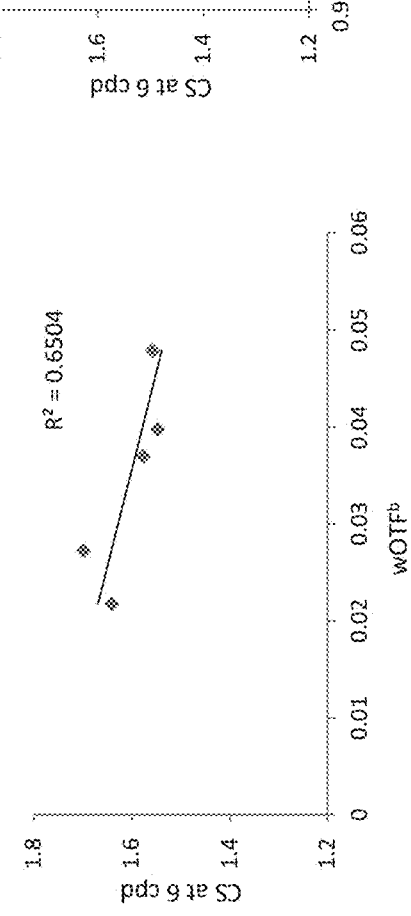

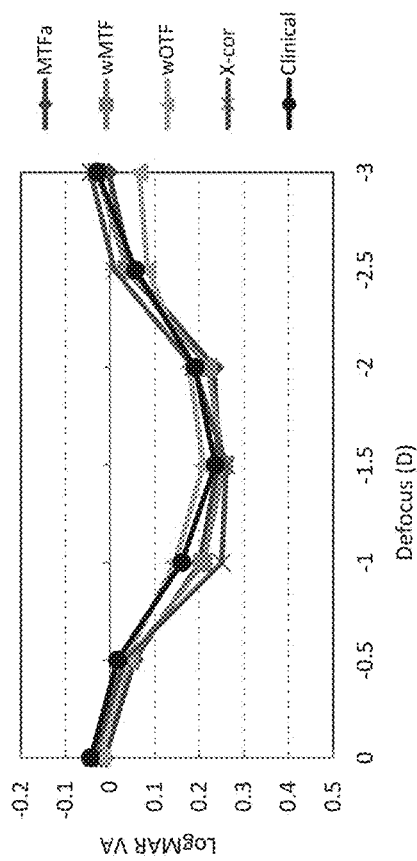
Figure 8A. IOL1
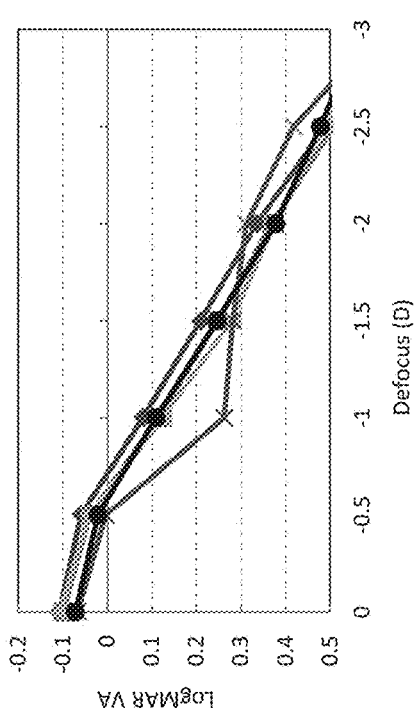
Figure 8B. IOL2

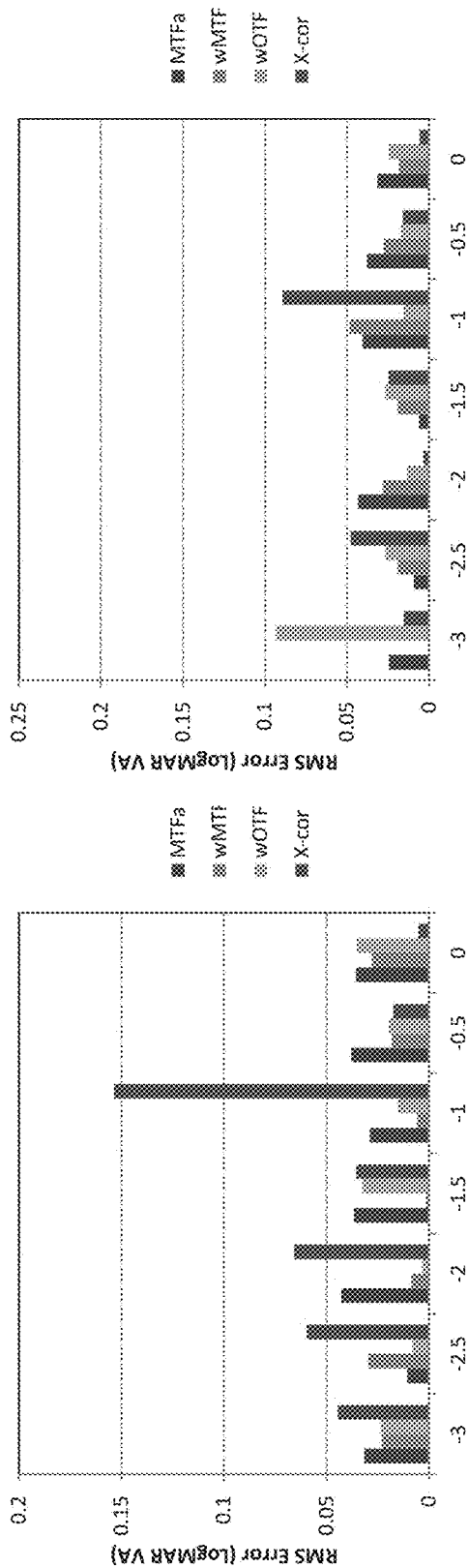

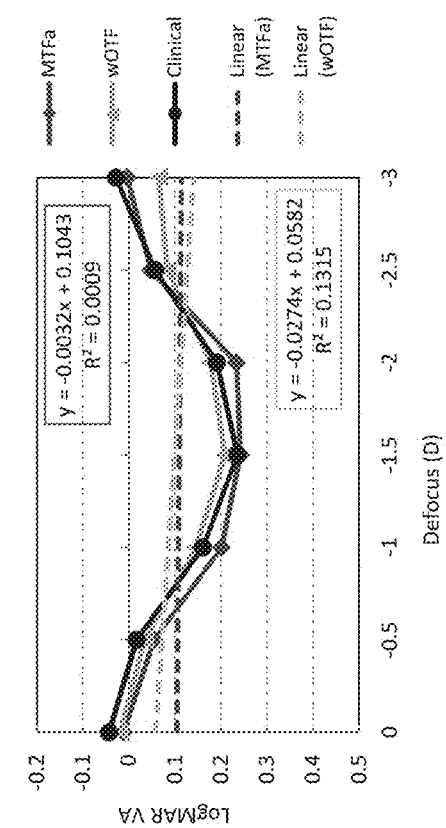
Figure 10B. IOL2
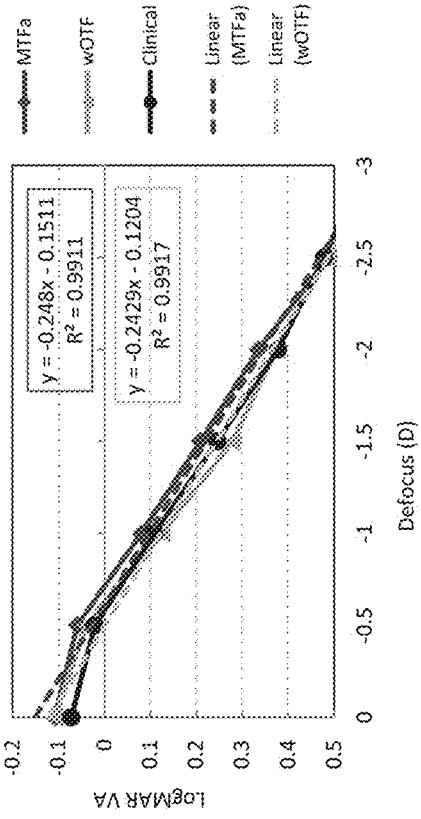
Figure 10A. IOL1

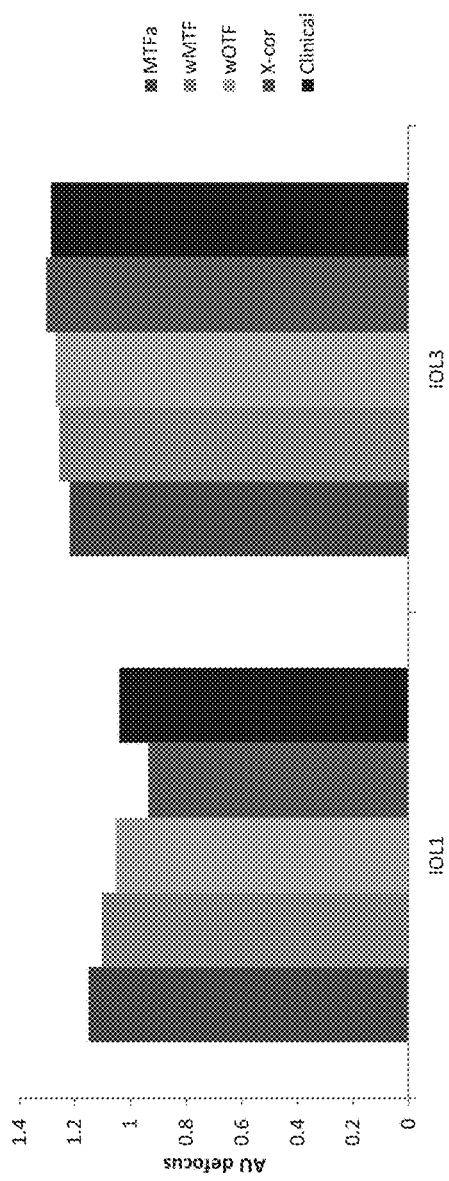

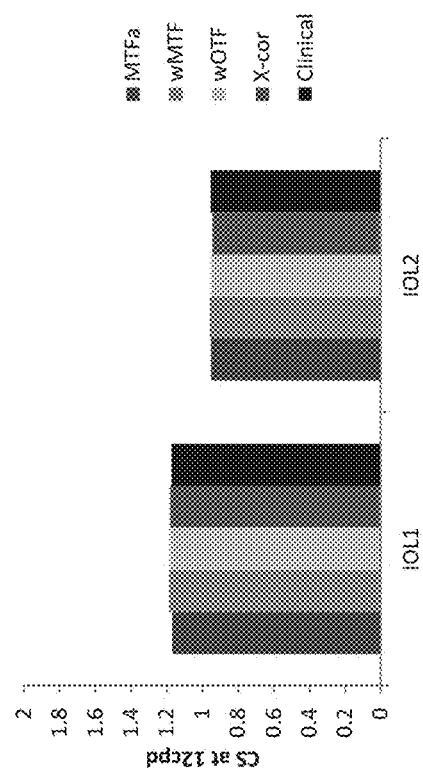
Figure 12A. CS at 6 cpd
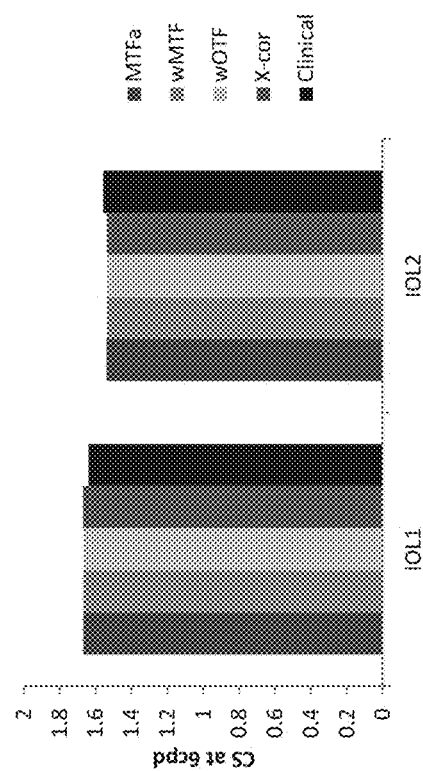
Figure 12B. CS at 12cpd

APPARATUS, SYSTEMS AND METHODS FOR IMPROVING VISUAL OUTCOMES FOR PSEUDOPHAKIC PATIENTS

This application is a non-provisional application and claims the benefit under 35 U.S.C. §119(e) of U.S. Provisional Application Ser. No. 62/087,585, filed Dec. 4, 2014, which is incorporated herein in its entirety as if fully set forth.

BACKGROUND OF THE INVENTION

Field of the Invention

This application is related to systems and methods for establishing expected clinical performance of an intraocular lens (IOL) when implanted in the eye.

Description of the Related Art

Retinal image quality of intraocular lenses when implanted in the eye of a patient can be estimated from different metrics obtained from bench-top optical measurements. Many of these metrics are obtained from bench-top optical measurements performed at the best focus of the IOL and at one or a few spatial frequencies and thus can be unreliable in predicting the performance when implanted in the eye and at non-peak focalities. Accordingly, it would be desirable to develop new techniques to reliably predict the performance of an IOL when implanted in the eye for different vergences, including distance, intermediate and/or near.

SUMMARY OF THE INVENTION

The systems and methods disclosed herein are configured to obtain or output metrics that can predict the clinical performance of an IOL when implanted in the eye. The metrics can be obtained from pre-clinical measurements of the IOL performed by a bench-top optical system. As one application, the systems and methods can output metrics that improve prediction of visual performance at focalities other than for distance vision, e.g., for intermediate vision. For example, the metrics discussed herein can predict the visual acuity and/or contrast sensitivity at different spatial frequencies of an IOL when implanted in the eye for different defocus positions (e.g. position at which the defocus is between 0 D and −3 D) and therefore to define the depth of focus provided by a particular lens design. The metrics described herein can characterize an average clinical performance of the IOL once implanted in the eye for a range of defocus positions, e.g., for intermediate vision.

The metrics described herein can be obtained for a range of spatial frequencies by comparing a reference image and the image obtained by the IOL at one defocus position (e.g., the best focus position) or a plurality of defocus positions. For example, the metrics can be inclusive of spatial frequencies between about 0 cycles per mm and about 50 cycles per mm, or about 0 cycles per mm and about 100 cycles per mm, or about 0 cycles per mm and about 200 cycles per mm. The plurality of defocus positions in the near vision distance range, the intermediate vision distance range or the distance vision distance range.

The metrics described herein improve the clinical prediction from preclinical data of the current state of art (modulation transfer function at a single spatial frequency). The metrics described herein can be used to rank the visual performance of different IOL designs and thus can be used to select IOLs that would provide optical performance that would best suit the needs of a patient when implanted in the eye of the patient. The metrics described herein can also be used to perform pre-clinical assessment of safety and efficacy of new IOL designs and select which among the new IOL designs can be used in clinical trials. The metrics described herein can also be used as a design tool to improve the performance of new and existing IOLs. The metrics described herein can be used for development and optimization of, for example, monofocal lenses, enhanced monofocal lenses, extended depth of focus lenses, multifocal lenses, extended range of vision lenses. The metrics described herein can also be used to develop new categories of IOLs.

Preferred embodiments include an optical system configured to predict clinical visual performance of an intraocular lens (IOL), the system comprising: a measurement device configured to acquire a plurality of images of a target including objects with different spatial frequencies and obtain modulation transfer function (MTF) and/or phase transfer function (PTF) at different spatial frequencies for different defocus positions of the IOL in a vision range from the acquired plurality of images, the measurement device comprising a processor configured to execute programmable instructions stored in a non-transitory computer storage medium to calculate at least one of: an area under the MTF (MTFa) for different spatial frequencies for each of the different defocus positions; a cross correlation coefficient (X-cor) for the acquired plurality of images at each of the different defocus positions; a weighted MTF (wMTF) corresponding to the area under the weighted MTF for each of the different spatial frequencies for each of the different defocus positions; or a weighted OTF (wOTF) corresponding to the area under the weighted OTF for each of the different spatial frequencies for each of the different defocus positions; and obtain a correlation with clinical data that predicts the VA at different defocus positions of the intraocular lens (IOL).

The measurement device may comprise of a reference image illuminated by a light source and an imaging system including a pupil. The computing device may be configured to simulate the plurality of images using models for the target and the IOL. The objects may have spatial frequencies between about 0 cycles per mm (cpmm) and 150 cpmm. The target may be selected from the group consisting of: an optotype; a slit; a 1951 USAF picture chart; and a subset of bars from a 1951 USAF picture chart. The light source may be a white light source and the pupil may have a size between 1 mm and 6 mm.

Another preferred embodiment includes an optical system configured to predict clinical visual performance of an intraocular lens (IOL), the system comprising a measurement device configured to acquire a plurality of images of a target including objects with different spatial frequencies and obtain modulation transfer function (MTF) and/or phase transfer function (PTF) at different spatial frequencies for different defocus positions of the IOL in a vision range from the acquired plurality of images, the measurement device comprising a processor configured to execute programmable instructions stored in a non-transitory computer storage medium to calculate at least one preclinical metric selected from: an area under the MTF (MTFa) for different spatial frequencies for each of the different defocus positions; a cross correlation coefficient (X-cor) for the acquired plurality of images at each of the different defocus positions; a weighted MTF (wMTF) corresponding to the area under the weighted MTF for each of the different spatial frequencies for each of the different defocus positions; and a weighted OTF (wOTF) corresponding to the area under the weighted OTF for each of the different spatial frequencies for each of the different defocus positions; and obtain a simulated VA at different defocus positions of the intraocular lens (IOL) from a previous correlation with clinical data that predicts the VA in different IOL models.

The system may also obtain a simulated CS at 6 cpd of the intraocular lens (IOL) from a previous correlation with clinical data that predicts the CS at 6 cpd in different IOL models. Further the system may obtain a simulated CS at 12 cpd of the intraocular lens (IOL) from a previous correlation with clinical data that predicts the CS at 12 cpd in different IOL models. The maximum of the simulated VA may be the best focus position of the metric and may be used to define the depth of focus of each evaluated IOL design. The simulated VA and CS may be used to set preclinical levels related to clinical effectiveness and safety requirements. The objects may have spatial frequencies between about 0 cycles per mm (cpmm) and 150 cpmm. The target may be selected from the group consisting of: an optotype; a slit; a 1951 USAF picture chart; and a subset of bars from a 1951 USAF picture chart. The target may be illuminated by a white light source and imaged by an imaging system including a 3 mm pupil. The simulated VA may be calculated from the at least one preclinical metric can be fit with a function, the fitted function associated with a slope and a correlation coefficient. The processor may be configured to calculate a degree of monotonic decrease, the monotonic decrease being a product of the slope and the correlation coefficient of the fitted function. The degree of monotonic decrease of simulated VA may be used to rank different IOL types. The processor may be configured to calculate a degree of tolerance to refractive errors, the tolerance to refractive errors being related to the slope of the fitted function in a determined defocus range. The simulated CS at 6 cpd calculated from the at least one preclinical metric may be fit with a function, the fitted function associated with a slope and a correlation coefficient. The processor may be configured to calculate a degree of tolerance to refractive errors, the tolerance to refractive errors being related to the slope of the fitted function in a determined defocus range. The simulated CS at 12 cpd may be calculated from the at least one preclinical metric can be fit with a function, the fitted function associated with a slope and a correlation coefficient. The processor may be configured to calculate a degree of tolerance to refractive errors, the tolerance to refractive errors being related to the slope of the fitted function in a determined defocus range.

Methods further include a method for evaluating the average visual performance for a defocus range using a metric based on the area under the through-focus visual acuity curve measured clinically. Additionally, a method for optimizing the cross correlation coefficient by correcting for magnification differences, average intensity levels and position shifts of the images is contemplated.

Another preferred embodiment includes optical system configured to predict the clinical visual performance of an intraocular lens (IOL) at an intermediate vision distance, the system comprising a measurement device configured to acquire a plurality of images of a target including objects with different spatial frequencies and obtain modulation transfer function (MTF) and/or phase transfer function (PTF) at different spatial frequencies for different defocus positions of the IOL in the intermediate distance vision from the acquired plurality of images, the measurement device comprising a processor configured to execute programmable instructions stored in a non-transitory computer storage medium to calculate at least one of: an area under the MTF (MTFa) for different spatial frequencies for each of the different defocus positions; a cross correlation coefficient (X-cor) for the acquired plurality of images at each of the different defocus positions; a weighted MTF (wMTF) corresponding to the area under the weighted MTF for each of the different spatial frequencies for each of the different defocus positions; or a weighted OTF (wOTF) corresponding to the area under the weighted OTF for each of the different spatial frequencies for each of the different defocus positions; and calculate at least one of: an area under the MTFa (AU MTFa) for the different defocus positions; an area under the X-cor (AU X-cor) for the different defocus positions; an area under the wMTF (AU wMTF) for the different defocus positions; or an area under the wOTF (AU wOTF) for the different defocus positions.

The processor may be further configured to obtain a correlation with clinical data that predicts the AU Defocus curve of the intraocular lens (IOL). The processor may be further configured to obtain a simulated AU Defocus Curve at different defocus positions of the intraocular lens (IOL) from a previous correlation with clinical data that predicts the intermediate performance in different IOL models. The simulated AU Defocus curve may be used to rank the intermediate performance of different IOL models. The objects may have spatial frequencies between about 0 cycles per mm (cpmm) and 150 cpmm. The target may be selected from the group consisting of: an optotype; a slit; a 1951 USAF picture chart; and a subset of bars from a 1951 USAF picture chart.

The target may be imaged by an imaging system including a 3 mm pupil.

A system is also contemplated for optimizing a clinical implementation of an ophthalmic lens, wherein one of the above methods or systems is employed. A method for optimizing the design of an intraocular lens is further envisioned, comprising of one of the above methods or systems. The above metric may be combined with other metrics using the equation $$\text{Metric}_{new} = \sum_{i=1}^{n} \text{Metric}(i)$$

or the equation $$\text{Metric}_{new} = f(\text{Metric}_1, \text{Metric}_2, \ldots, \text{Metric}_n),$$

wherein the function f can be a linear or a non-linear equation. The correlation between the metric and clinical data from historical lens designs may be used to fine-tune the metric for the prediction of new lens designs.

Additional embodiments include a method of predicting clinical visual performance of an intraocular lens (IOL), the method comprising acquiring a plurality of images of a target including objects with different spatial frequencies obtaining modulation transfer function (MTF) and/or phase transfer function (PTF) at different spatial frequencies for different defocus positions of the IOL in a vision range from the acquired plurality of images; and under the control of a hardware computing device calculating at least one of: an area under the MTF (MTFa) for different spatial frequencies for each of the different defocus positions; a cross correlation coefficient (X-cor) for the acquired plurality of images at each of the different defocus positions; a weighted MTF (wMTF) corresponding to the area under the weighted MTF for each of the different spatial frequencies for each of the different defocus positions; or a weighted OTF (wOTF) corresponding to the area under the weighted OTF for each of the different spatial frequencies for each of the different defocus positions; and obtaining a correlation with clinical data that predicts the VA at different defocus positions of the intraocular lens (IOL); obtaining a correlation with clinical data that predicts the CS at 6 cpd of the intraocular lens (IOL); and obtaining a correlation with clinical data that predicts the CS at 12 cpd of the intraocular lens (IOL).

Additional embodiments include a method of predicting clinical visual performance of an intraocular lens (IOL), the method comprising acquiring a plurality of images of a target including objects with different spatial frequencies; obtaining modulation transfer function (MTF) and/or phase transfer function (PTF) at different spatial frequencies for different defocus positions of the IOL in a vision range from the acquired plurality of images; and under the control of a hardware computing device calculating at least one of: an area under the MTF (MTFa) for different spatial frequencies for each of the different defocus positions; a cross correlation coefficient (X-cor) for the acquired plurality of images at each of the different defocus positions; a weighted MTF (wMTF) corresponding to the area under the weighted MTF for each of the different spatial frequencies for each of the different defocus positions; and a weighted OTF (wOTF) corresponding to the area under the weighted OTF for each of the different spatial frequencies for each of the different defocus positions; and obtaining a simulated VA at different defocus positions of the intraocular lens (IOL) from a previous correlation with clinical data that predicts the VA in different IOL models; obtaining a simulated CS at 6 cpd of the intraocular lens (IOL) from a previous correlation with clinical data that predicts the CS at 6 cpd in different IOL models; and obtaining a simulated CS at 12 cpd of the intraocular lens (IOL) from a previous correlation with clinical data that predicts the CS at 12 cpd in different IOL models Additional embodiments include a method of predicting the clinical visual performance of an intraocular lens (IOL) at an intermediate vision distance, the method comprising: acquiring a plurality of images of a target including objects with different spatial frequencies; obtain modulation transfer function (MTF) and/or phase transfer function (PTF) at different spatial frequencies for different defocus positions of the IOL in the intermediate distance vision range from the acquired plurality of images; and under the control of a hardware computing device calculating at least one of: an area under the MTF (MTFa) for different spatial frequencies for each of the different defocus positions; a cross correlation coefficient (X-cor) for the acquired plurality of images at each of the different defocus positions; a weighted MTF (wMTF) corresponding to the area under the weighted MTF for each of the different spatial frequencies for each of the different defocus positions; or a weighted OTF (wOTF) corresponding to the area under the weighted OTF for each of the different spatial frequencies for each of the different defocus positions; and calculating at least one of: an area under the MTFa (AU MTFa) for the different defocus positions; an area under the X-cor (AU X-cor) for the different defocus positions; an area under the wMTF (AU wMTF) for the different defocus positions; or an area under the wOTF (AU wOTF) for the different defocus positions.

Further embodiments include a method for predicting visual acuity, in which the visual acuity is a power function of a metric. It is envisioned that the visual acuity may be a power function of one of the above metrics. The power function may also have the form VA(x)=ax^b+c. where VA is the clinical visual acuity and x is the metric. In the preceding formula, a may vary between 0 and 3, b may vary between −3 and 0, and c may vary between −1 and 0.

Further embodiments include a method for predicting contrast sensitivity, in which the contrast sensitivity is a power function of a metric. The contrast sensitivity may be a power function of one of the above metrics. The power function may also have the form CS(x)=ax^b+c. where CS is the clinical contrast sensitivity and x is the metric. In the preceding formula a may vary between −60 and 20, b may vary between −3 and 4, and c may vary between −15 and 3.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 1A illustrates the comparison between the high contrast binocular visual acuity measured in patients bilaterally implanted with the same IOLs and the MTFa preclinical metric integrated between 0 cycles per mm to 50 cycles per mm at different defocus positions between about 0 D and about −3.0 D.

FIG. 1B illustrates the comparison between the visual acuity measured in patients bilaterally implanted with the same IOLs and wMTF preclinical metric integrated between 0 cycles per mm to 150 cycles per mm at different defocus positions between about 0 D and about −3.0 D.

FIG. 1C illustrates the comparison between the visual acuity measured in patients bilaterally implanted with the same IOLs and wOTF preclinical metric integrated between 0 cycles per mm to 150 cycles per mm at different defocus positions between about 0 D and about −3.0 D.

FIG. 1D illustrates the comparison between the visual acuity measured in patients bilaterally implanted with the same IOLs and the cross-correlation coefficient (X-cor) obtained from 1951 USAF optotype at different defocus positions between about 0 D and about −3.0 D.

FIG. 3A illustrates the comparison between the visual acuity measured in patients bilaterally implanted with the same IOL and MTF at a single spatial frequency of 50 cycles per mm between 0 D to −3 D. FIG. 3B illustrates the comparison between the visual acuity measured in patients bilaterally implanted with the same IOL and MTF at a single spatial frequency of 100 cycles per mm between 0 D to −3 D. Values under the repeatability limit of the measurements according to the ISO standard (0.09) are plotted in red while values above 0.09 are plotted in blue.

FIG. 4A illustrates the comparison between the area under the defocus curve measured in patients bilaterally implanted with the same IOLs integrated over the intermediate range (at different defocus positions between about −0.5 D to −2.0 D) and the area under the MTFa preclinical metric integrated between 0 cycles per mm to 50 cycles per mm for the same defocus range.

FIG. 4B illustrates the comparison between the area under the defocus curve measured in patients bilaterally implanted with the same IOLs integrated over the intermediate range and the area under the wMTF preclinical metric integrated between 0 cycles per mm to 150 cycles per mm for the same defocus range.

FIG. 4C illustrates the comparison between the area under the defocus curve measured in patients bilaterally implanted with the same IOLs integrated over the intermediate range and the area under the wOTF preclinical metric integrated between 0 cycles per mm to 150 cycles per mm for the same defocus range.

FIG. 4D illustrates the comparison between the area under the defocus curve measured in patients bilaterally implanted with the same IOLs integrated over the intermediate range and the area under the cross-correlation coefficient (X-cor) obtained from 1951 USAF optotype within the same defocus range.

FIG. 5A illustrates the comparison between the contrast sensitivity at 6 cycles per degree (cpd) measured in patients bilaterally implanted with the same IOLs and the MTFa preclinical metric integrated between 0 cycles per mm to 50 cycles per mm at 0 D defocus.

FIG. 5B illustrates the comparison between the contrast sensitivity at 6 cpd measured in patients bilaterally implanted with the same IOLs and the wMTF preclinical metric integrated between 0 cycles per mm to 150 cycles per mm at 0 D defocus.

FIG. 5C illustrates the comparison between the contrast sensitivity at 6 cpd measured in patients bilaterally implanted with the same IOLs and the wOTF preclinical metric integrated between 0 cycles per mm to 150 cycles per mm at 0 D defocus.

FIG. 5D illustrates the comparison between the contrast sensitivity at 6 cpd measured in patients bilaterally implanted with the same IOLs and the cross-correlation coefficient (X-cor) obtained from 1951 USAF optotype at 0 D defocus.

FIG. 8A shows a comparison between the simulated VA calculated for a particular IOL model and the clinical VA measured in patients bilaterally implanted with the same IOL model. FIG. 8B shows a comparison between the simulated VA calculated for a second IOL model and the clinical VA measured in patients bilaterally implanted with the second IOL model.

FIG. 9A shows the absolute difference between the simulated VA calculated for a first IOL model and the clinical VA measured in patients bilaterally implanted with the first IOL model. FIG. 9B shows the absolute difference between the simulated VA calculated for a second IOL model and the clinical VA measured in patients bilaterally implanted with the second IOL model.

FIG. 10A shows linear fitting of the simulated VA for a first IOL model and the clinical VA measured in patients bilaterally implanted with the first IOL model. FIG. 10B shows linear fitting of the simulated VA for a second IOL model and the clinical VA measured in patients bilaterally implanted with the second IOL model.

FIG. 11 shows the simulated area under the defocus curve calculated from different preclinical metrics for two IOL models as compared to the area under the measured defocus curve in patients implanted with the same IOLs.

FIG. 12A shows the simulated CS at 6 cpd calculated from different preclinical metrics for two IOL models as compared to the clinical CS at 6 cpd measured in patients implanted with the same IOLs. FIG. 12B shows the simulated CS at 12 cpd calculated from different preclinical metrics for two IOL models as compared to the clinical CS at 12 cpd measured in patients implanted with the same IOLs.

DETAILED DESCRIPTION OF THE PREFERRED EMBODIMENT

Figure 2:
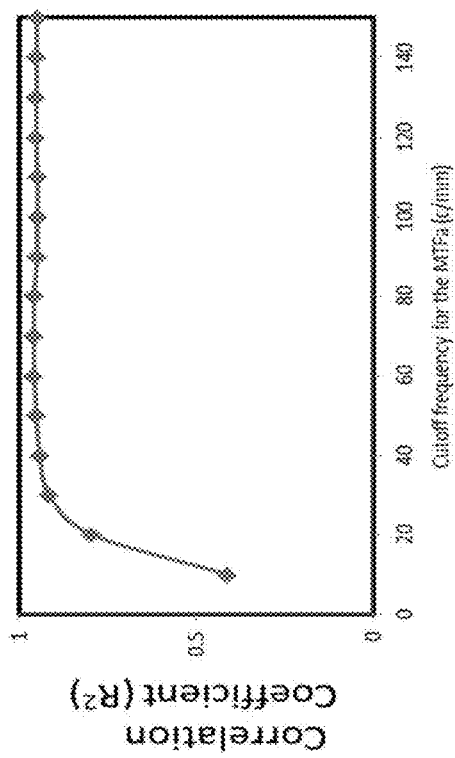
FIG. 2 illustrates the correlation coefficients between clinical VA and MTFa as a function of the cutoff spatial frequency used to calculate the MTFa.

Each and every feature described herein, and each and every combination of two or more of such features, is included within the scope of the present invention provided that the features included in such a combination are not mutually inconsistent.

As used herein, the terms "about" or "approximately", when used in reference to a Diopter value of an optical power, mean within plus or minus 0.25 Diopter of the referenced optical power(s). As used herein, the terms "about" or "approximately", when used in reference to a percentage (%), mean within plus or minus one percent (±1%). As used herein, the terms "about" or "approximately", when used in reference to a linear dimension (e.g., length, width, thickness, distance, etc.) mean within plus or minus one percent (1%) of the value of the referenced linear dimension.

Pre-clinical optical performance of IOLs is currently assessed using modulation transfer function (MTF) values at a single spatial frequency between about 0 cycles per mm and about 100 cycles per mm. The Modulation Transfer Function (MTF), describing the resolution and performance of an optical system is the ratio of relative image contrast divided by relative object contrast. In other words MTF=Relative Image Contrast/Relative Object Contrast. Through focus visual acuity is clinically measured using optotypes that can be deconstructed into multiple spatial frequencies. All spatial frequencies contribute to the interpretation of these optotypes. For example, lower spatial frequencies can help characterize the performance of the IOLs in performing visual tasks under conditions of noise or blur. Accordingly, multiple spatial frequencies should be considered when evaluating the pre-clinical optical performance of the IOL so that the pre-clinical estimate matches the visual acuity of the IOL when implanted in the eye.

One such pre-clinical metric is the area under the through focus MTF curve captured for multiple spatial frequencies simultaneously (MTFa). The MTFa can be defined using equation 1 from 0 cycles per mm to 50 cycles per mm, where d determines the sampling size for preclinical measurements at each spatial frequency (f).

$$MTFa = \sum_{f=1}^{50\ cpmm/d} \frac{d}{50} MTF(fd) \quad \text{Equation 1}$$

The MTFa can be integrated between 0 cycles per mm and 50 cycles per mm; between 0 cycles per mm and 100 cycles per mm; between 0 cycles per mm and 150 cycles per mm; between 5 cycles per mm and 150 cycles per mm; between 0 cycles per mm and 200 cycles per mm; or there between.

Another example of a pre-clinical metric that can predict the visual performance of an IOL when implanted bilaterally in a patient is the area under the weighted MTF (wMTF). The wMTF can be calculated for each defocus position by the area under the product of the threshold contrast sensitivity ($CS_{th}$) (as measured by Campbell and Green in 1965[1]) and the MTF measured in the optical bench for a range of spatial frequencies (equation 2) where d determines the sampling size for preclinical measurements at each spatial frequency (f).

$$wMTF = \sum_{f=1}^{150\ cpmm/d} \frac{d}{150} MTF(fd) CS_{th}(fd) \quad \text{Equation 2}$$

For example, the wMTF can be integrated between 0 cycles per mm and 50 cycles per mm; between 0 cycles per mm and 100 cycles per mm; between 0 cycles per mm and 150 cycles per mm; between 0 cycles per mm and 200 cycles per mm; or there between.

Another example of metric that can predict the visual performance of an IOL when implanted bilaterally in a patient is the area under the weighted optical transfer function (wOTF). The wOTF can be calculated for each defocus position as described in equation 3 where d determines the sampling size of the spatial frequency (f), PTF is the phase transfer function measured in the optical bench and the $CS_{th}$ the threshold contrast sensitivity as measured by Green and Campbell (1965) Campbell F W, Green D G. Optical and retinal factors affecting visual resolution. J Physiol. 1965; 181(3):576-93.

$$wOTF = \sum_{f=1}^{150\ cpmm/d} \frac{d}{150} MTF(fd) CS_{th}(fd) \cos(PTF(fd)) \quad \text{Equation 3}$$

The wOTF can be integrated between 0 cycles per mm and 50 cycles per mm; between 0 cycles per mm and 100 cycles per mm; between 0 cycles per mm and 150 cycles per mm; between 0 cycles per mm and 200 cycles per mm; or there between.

Another example of a metric that is capable of predicting the visual performance of an IOL when binocularly implanted in a patient is the cross correlation (X-cor) metric. The X-cor metric can be calculated by performing a convolution of a reference image and the image collected by a bench-top optical system for each defocus position, adjusting parameters of the collected image, such as for example, magnification, average intensity levels and position shifts of the collected images in order to yield the highest cross correlation coefficient. A reference image having a wide range of spatial frequencies and orientations can provide a better estimate of the visual performance. For example, the reference image can include the 1951 USAF resolution test chart, the USAF optical test pattern or other patterns and images used in optometry. In various implementations, the X-cor metric can be obtained by using, as reference image, a 1951 USAF picture chart measured on a bench-top optical system at the best focus for the ISO cornea for a 3 mm pupil at green light in water without IOL.

The MTFa, the wMTF, the wOTF and the X-cor metrics can predict the through focus visual acuity of an IOL when implanted bilaterally with sufficient accuracy. Therefore, and because these metrics correlate to clinical performance, their maximum is a valid best focus position, from which depth of focus can be defined, so that these metrics can be used to define the clinical depth of focus provided for a particular lens design from preclinical data measured in actual IOL samples. Alternatively, to evaluate if the through focus visual acuity provided by an IOL decreases monotonically from the best focus, the MD (monotonic decrease) parameter can be calculated using the visual acuity curves predicted by these metrics. The MD-parameter can be calculated by fitting the predicted visual acuity to a linear function from 0 D to −3 D. Without any loss of generality, the MD-parameter can refer to the product of the slope and the correlation coefficient ($R^2$) of the linear function. For example, monofocal lenses have a clear monotonic decrease of the visual acuity from the best focus which corresponds to very negative MD parameters.

In another embodiment, the predicted visual acuity can be fitted to a linear function for a smaller defocus range, i.e. between 0 D and −1.5 D or between 0 D and −1.0 D or between 0 D and −0.5 D. The range can also incorporate positive defocus values, so that the fitting can be performed between +0.5 D and −0.5 D. To evaluate if the lens is tolerant to refractive errors, a TRE (tolerance to refractive errors) parameter can be calculated using the through focus visual acuity or contrast sensitivity curves provided by these metrics. The TRE-parameter can be calculated by fitting the predicted visual acuity to a linear function from 0 D to −1.5 D or to −1.0 D or to −0.5 D. Without any loss of generality, the TRE-parameter can refer to the inverse of product of the slope and the correlation coefficient ($R^2$) of the linear function. In an alternative embodiment, the TRE-parameter can be defined as the inverse of the slope of the linear function. The more tolerant to refractive errors the lens is, the higher the TRE-parameter will be.

Another metric to evaluate the visual acuity over a range of defocus is the area under through focus visual acuity curve (AU Defocus curve) measured clinically in patients implanted with an IOL. The AU Defocus curve provides with a single value to estimate the average visual performance over a defocus range (e.g. from −2 D to −0.5 D to evaluate intermediate vision; from −0.5 D to 0 D to evaluate distance vision; from −3 D to −2 D to evaluate near vision; from −0.5 D to +0.5 D to evaluate tolerance to refractive errors). For a given defocus range, the AU Defocus curve is calculated by integrating the area under the through focus visual acuity measured clinically over that defocus range. The AU Defocus parameter can alternatively be calculated from the clinical through focus contrast sensitivity measured for one particular spatial frequency.

The AU Defocus curve over a defocus range (e.g. from −2 D to −0.5 D to evaluate intermediate vision) can be estimated from preclinical measurements by the area under the through focus MTFa (AU MTFa) for a given spatial frequency range (e.g. from 0 cycles per mm to 50 cycles per mm; from 0 cycles per mm to 100 cycles per mm). The AU MTFa, calculated from the preclinical through focus MTF measurements, provides with a single value to describe the average visual performance of a pseudophakic patient implanted with an IOL over a range of defocus.

Another metric that can predict the average visual performance over a range of defocus is the area under the through focus wMTF (AU wMTF) for that defocus range. The AU wMTF can be calculated by integrating the wMTF over a defocus range (e.g. between −2 D and −0.5 D to evaluate intermediate vision).

Another metric that can predict the average visual performance over a range of defocus is the area under the through focus (AU wOTF) for that defocus range. The AU wOTF can be calculated by integrating the wOTF over a defocus range (e.g. between −2 D and −0.5 D to evaluate intermediate vision).

Another metric that can predict the average visual performance of an IOL for a given defocus range from preclinical data is the area under the through focus X-cor (AU X-cor) for that defocus range. The AU X-cor can be calculated by integrating the X-cor curve over a defocus range (e.g. between −2 D and −0.5 D to evaluate intermediate vision). An implementation of a system and method of obtaining the different metrics discussed above is described below.

The MTFa, the wMTF, the wOTF can predict the distance contrast sensitivity (CS) at 6 and 12 cpd of an IOL when implanted bilaterally. Furthermore, AU MTFa, AU wMTF and AU wOTF can be used to predict the area under the contrast sensitivity through focus curve, providing an estimation of the contrast performance in the intermediate range.

Correlation Between Preclinical Metrics and Clinical Results

The correlation between the various metrics described in the previous section calculated for several different IOL models and the high contrast binocular visual acuity (VA) measured in patients implanted with the same IOL models is described below with reference to FIGS. 1A-4D. Preclinical metrics were calculated based on through focus/through frequency MTF, PTF and USAF images recorded for different defocus positions using the average corneal eye model that reflects the average corneal spherical aberration and chromatic aberration of the pseudophakic eye. Norrby, S., Piers, P., Campbell, C., van der Mooren, M. Model eyes for evaluation of intraocular lenses. Appl Opt. 2007; 46(26): 6595-605. These measurements were obtained using a bench-top optical system for different IOL models at 3 mm pupil in white light. The corresponding metric for each defocus position was correlated to the VA measured at the same vergence in patients implanted with the same IOL models. The function defined in Equation 4 can be used to fit the clinical VA (VA) and each of the preclinical metrics MTFa, wMTF, wOTF and X-cor (x) by optimizing the $R^2$ correlation coefficient. The parameters a, b and c may be optimized for each metric:

$$VA(x) = ax^b + c \quad \text{Equation 4}$$

FIG. 1A illustrates the comparison between the visual acuity measured in patients bilaterally implanted with the same IOLs and the preclinical metric MTFa integrated between 0 cycles per mm to 50 cycles per mm. at different defocus positions between about 0 D and about −3.0 D. The x-axis represents the preclinical metric to the b power. The coefficients of equation 4 a, b and c that provide the best fitting of the preclinical metric MTFa are shown in Table 1.

TABLE 1

$R^2$ and coefficients (a, b and c) than best fit the clinical VA with the preclinical metrics MTFa, wMTF, wOTF and X-cor using equation 4.

|   | MTFa | wMTF | wOTF | X-cor |
|---|------|------|------|-------|
| $R^2$ | 0.951 | 0.959 | 0.935 | 0.893 |
| a | 0.078414 | 2.065996 | 1.0865 | 0.130328 |
| b | −1.00019 | −0.75199 | −0.3646 | −1.42647 |
| c | −0.2072 | −0.19493 | −0.35135 | −0.21744 |

The MTFa was calculated for spatial frequencies up to 50 cpmm. This value was chosen because the correlation coefficient between the clinical VA and the MTFa reaches a plateau (FIG. 2). Therefore, adding higher spatial frequencies into the calculation of the MTFa does not increase the accuracy of the metric, only the noise due to potential measurement errors.

For comparison, FIG. 3A illustrates the comparison between the high contrast binocular visual acuity (VA) measured clinically for different IOLs and the MTF at a single spatial frequency of about 50 cpmm between about 0 D and about −3.0 D. FIG. 3B illustrates the comparison between the binocular visual acuity (VA) measured clinically for different IOLs and the MTF at a single spatial frequency of about 100 cpmm for the same defocus positions. Values under the repeatability limit of the measurements according to the ISO standard (0.09) (ISO 11979-2: 2014-Annex C.5). are plotted in red while values above 0.09 are plotted in blue. As noted from FIGS. 3A and B, most MTF values at 50 cpmm and 100 cpmm are less than 0.09 which is the repeatability limit of the measurements according to the abovementioned ISO standard. The correlation between MTF at a single spatial frequency and the measured visual acuity characterized by the coefficient $R^2$ is 0.80 for 50 cpmm and 0.68 for 100 cpmm. As noted from FIG. 1A, the correlation ($R^2$) between MTFa integrated for different spatial frequencies and the measured visual acuity is 0.95. Thus, MTFa provides a better estimate of the optical performance of the IOL when implanted in the patient's eye than MTF at a single frequency.

FIG. 1B illustrates the comparison between the high contrast binocular visual acuity measured in patients bilaterally implanted with the same IOLs and wMTF (indicated by solid diamonds) preclinical metric integrated between 0 cycles per mm to 150 cycles per mm at different defocus positions between about 0 D and about −3.0 D. The x-axis represents the preclinical metric to the b power. The coefficients of equation 4 a, b and c that provide the best fitting of the preclinical metric wMTF are shown in Table 1.

FIG. 1C illustrates the comparison between the high contrast binocular visual acuity measured in patients bilaterally implanted with the same IOLs and wOTF (indicated by solid diamonds) preclinical metric integrated between 0 cycles per mm to 150 cycles per mm at different defocus positions between about 0 D and about −3.0 D. The x-axis represents the preclinical metric to the b power. The coefficients of equation 4 a, b and c that provide the best fitting of the preclinical metric wOTF are shown in Table 1.

FIG. 1D illustrates the comparison between the high contrast binocular visual acuity measured in patients bilaterally implanted with the same IOLs and the cross-correlation metric (X-cor) obtained from 1951 USAF optotype at different defocus positions between about 0 D and about −3.0 D. The x-axis represents the preclinical metric to the b power. The coefficients of equation 4 a, b and c that provide the best fitting of the preclinical metric X-cor are shown in Table 1.

The various metrics illustrated in FIGS. 1A-1D showed a high correlation with clinical defocus curves ($R^2>0.89$). Therefore, clinical VA can be predicted at different defocus positions between about 0 D and about −3.0 D from these correlations, using any of the preclinical metrics previously described. The clinical VA predicted from preclinical metrics will be herein referred as 'simulated VA'.

FIG. 4A illustrates the comparison between the area under the high contrast visual acuity defocus curve measured in patients bilaterally implanted with the same IOLs integrated over the intermediate range (at different defocus positions between about −0.5 D to −2.0 D) and the area under the preclinical metric MTFa integrated between 0 cycles per mm to 50 cycles per mm (indicated by solid diamonds). The data points associated with the preclinical metric MTFa integrated between 0 cycles per mm to 50 cycles per mm (indicated by solid diamonds) are fit with a linear curve 405a.

FIG. 4B illustrates the comparison between the area under the defocus curve measured in patients bilaterally implanted with the same IOLs integrated over the intermediate range (at different defocus positions between about −0.5 D to −2.0 D) and the area under the wMTF (indicated by solid diamonds). The data points associated with the preclinical metric wMTF (indicated by solid diamonds) are fit with a linear curve 405b.

FIG. 4C illustrates the comparison between the area under the defocus curve measured in patients bilaterally implanted with the same IOLs integrated over the intermediate range (at different defocus positions between about −0.5 D to −2.0 D) and the area under the wOTF (indicated by solid diamonds). The data points associated with the preclinical metric wOTF (indicated by solid diamonds) are fit with a linear curve 405b FIG. 4D illustrates the comparison between the area under the defocus curve measured in patients bilaterally implanted with the same IOLs integrated over the intermediate range and the area under the cross-correlation metric (X-cor) obtained from 1951 USAF optotype within the same defocus range. The data points associated with the metric X-cor are fit with a linear curve 405b.

The various metrics illustrated in FIGS. 4A-4D showed a high correlation with clinical AU defocus curves ($R^2>0.796$). Therefore, clinical AU high contrast defocus curves can be predicted at different defocus positions between about −0.5 D and about −2.0 D using any of the preclinical metrics previously described above. The AU high contrast defocus curve predicted from preclinical metrics will be herein referred as 'simulated AU Defocus curve'.

The correlation between the preclinical metrics MTFa, wMTF, wOTF and X-cor described in the previous section calculated for several different IOL models and the clinical CS at 6 and 12 cycles per degree (cpd) measured in patients implanted with the same IOL models is described below with reference to FIGS. 5A-6D. Preclinical metrics were calculated based on through frequency MTF and PTF recorded for 0 D of defocus. These measurements were obtained using a bench-top optical system for different IOL models at 3 mm pupil in white light. The corresponding metric for each defocus position was correlated to the CS at 6 and 12 cpd measured at the same vergence in patients bilaterally implanted with the same IOL models in mesopic conditions without glare. The function defined in Equation 5 can used to fit the clinical CS (CS) and the preclinical metrics MTFa, wMTF, wOTF and X-cor (x) by optimizing the $R^2$ correlation coefficient. The parameters a, b and c may be optimized for each metric:

$$CS(x)=ax^b+c \qquad \text{Equation 5}$$

FIG. 5A illustrates the comparison between the clinical CS at 6 cpd measured in patients bilaterally implanted with the same IOLs and the preclinical metric MTFa at 0 D defocus. The x-axis represents the preclinical metric to the b power. The coefficients of equation 5 a, b and c, that provide the best fitting of the preclinical metric MTFa, are shown in Table 2.

TABLE 2

$R^2$ and coefficients (a, b and c) than best fit the clinical CS at 6 cpd with the preclinical metrics MTFa, wMTF and wOTF using equation 5.

|  | MTFa | wMTF | wOTF | X-cor |
|---|---|---|---|---|
| $R^2$ | 0.747 | 0.688 | 0.650 | 0.629 |
| a | −0.03191 | −59.7651 | −4.9608 | 4.013639 |
| b | −1.90106 | −1.75212 | −0.93507 | 0.27834 |
| c | 1.720074 | 1.71499 | 1.77662 | −2.23111 |

FIG. 5B illustrates the comparison between the clinical CS at 6 cpd measured in patients bilaterally implanted with the same IOLs and the preclinical metric wMTF at 0 D defocus. The x-axis represents the preclinical metric to the b power. The coefficients of equation 5 a, b and c, that provide the best fitting of the preclinical metric wMTF, are shown in Table 2.

FIG. 5C illustrates the comparison between the clinical CS at 6 cpd measured in patients bilaterally implanted with the same IOLs and the preclinical metric wOTF at 0 D defocus. The x-axis represents the preclinical metric to the b power. The coefficients of equation 5 a, b and c, that provide the best fitting of the preclinical metric wOTF, are shown in Table 2.

FIG. 5D illustrates the comparison between the clinical CS at 6 cpd measured in patients bilaterally implanted with the same IOLs and the preclinical metric X-cor at 0 D defocus. The x-axis represents the preclinical metric to the b power. The coefficients of equation 5 a, b and c, that provide the best fitting of the preclinical metric X-cor, are shown in Table 2.

Figure 6A:
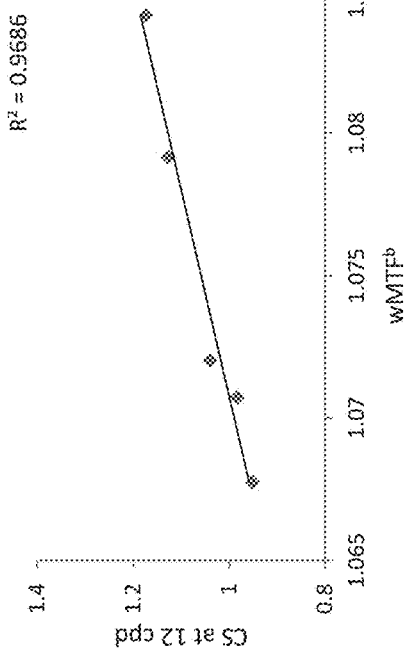
FIG. 6A illustrates the comparison between the contrast sensitivity at 12 cpd measured in patients bilaterally implanted with the same IOLs and the MTFa preclinical metric integrated between 0 cycles per mm to 50 cycles per mm at 0 D defocus.

FIG. 6A illustrates the comparison between the clinical CS at 12 cpd measured in patients bilaterally implanted with the same IOLs and the preclinical metric MTFa integrated between 0 cycles per mm to 50 cycles per mm at 0 D defocus. The x-axis represents the preclinical metric to the b power. The coefficients of equation 5 a, b and c, that provide the best fitting of the preclinical metric MTFa, are shown in Table 3.

TABLE 3

$R^2$ and coefficients (a, b and c) than best fit the clinical CS at 12 cpd with the preclinical metrics MTFa, wMTF and wOTF using equation 5.

|  | MTFa | wMTF | wOTF | X-cor |
|---|---|---|---|---|
| $R^2$ | 0.970 | 0.969 | 0.974 | 0.985 |
| a | −0.10183 | 13.89135 | 2.010493 | 0.955806 |
| b | −1.38586 | 0.019724 | 0.096027 | 3.571574 |
| c | 1.31097 | −13.8744 | −1.79611 | 0.51569 |

Figure 6C:
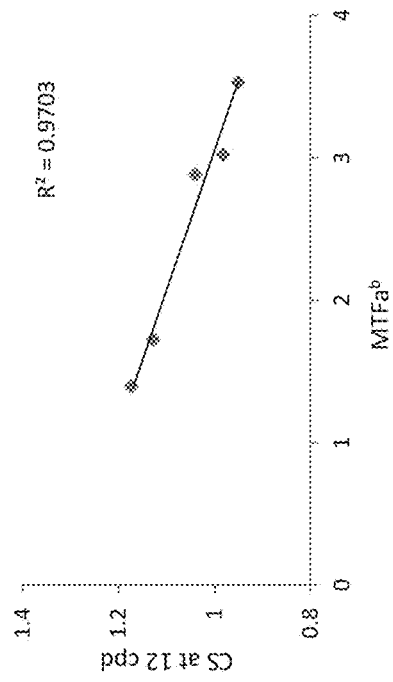
FIG. 6C illustrates the comparison between the contrast sensitivity at 12 cpd measured in patients bilaterally implanted with the same IOLs and the wOTF preclinical metric integrated between 0 cycles per mm to 150 cycles per mm at 0 D defocus.
Figure 6B:
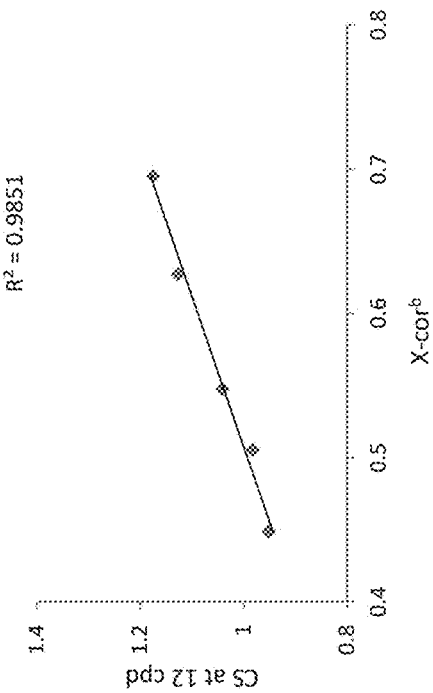
FIG. 6B illustrates the comparison between the contrast sensitivity at 12 cpd measured in patients bilaterally implanted with the same IOLs and the wMTF preclinical metric integrated between 0 cycles per mm to 150 cycles per mm at 0 D defocus.

FIG. 6B illustrates the comparison between the clinical CS at 12 cpd measured in patients bilaterally implanted with the same IOLs and the preclinical metric wMTF at 0 D defocus. The x-axis represents the preclinical metric to the b power. The coefficients of equation 5 a, b and c, that provide the best fitting of the preclinical metric wMTF, are shown in Table 3.

FIG. 6C illustrates the comparison between the clinical CS at 12 cpd measured in patients bilaterally implanted with the same IOLs and the preclinical metric wOTF at 0 D defocus. The x-axis represents the preclinical metric to the b power. The coefficients of equation 5 a, b and c, that provide the best fitting of the preclinical metric wOTF, are shown in Table 3.

Figure 6D:
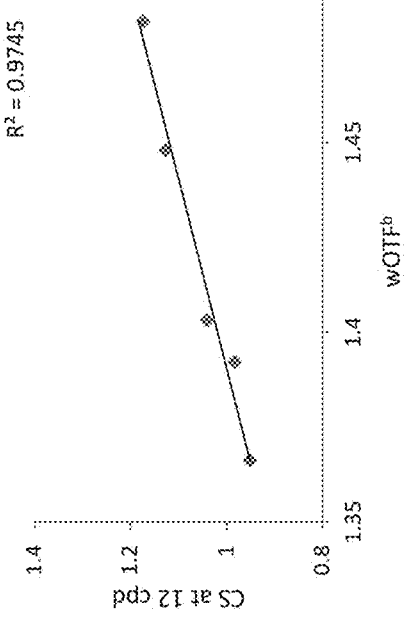
FIG. 6D illustrates the comparison between the contrast sensitivity at 12 cpd measured in patients bilaterally implanted with the same IOLs and the cross-correlation coefficient (X-cor) obtained from 1951 USAF optotype at 0 D defocus.

FIG. 6D illustrates the comparison between the clinical CS at 12 cpd measured in patients bilaterally implanted with the same IOLs and the preclinical metric X-cor at 0 D defocus. The x-axis represents the preclinical metric to the b power. The coefficients of equation 5 a, b and c, that provide the best fitting of the preclinical metric X-cor, are shown in Table 3.

It is noted that the correlation between clinical data and preclinical metrics will change if preclinical metrics are performed for different optical conditions (e.g. green/white light, 3 mm/5 mm aperture, etc.).

Example of Characterizing the Optical Performance of IOLs Using the Metrics

In one example of the systems and methods, the performance of two IOLs was compared. One of the IOLs included was aspheric monofocal IOL (referred to herein as IOL1). Another IOL also included was one aspheric multifocal lens, with an add power of +4.00 in the IOL plane (referred to herein IOL2)

Figure 7:
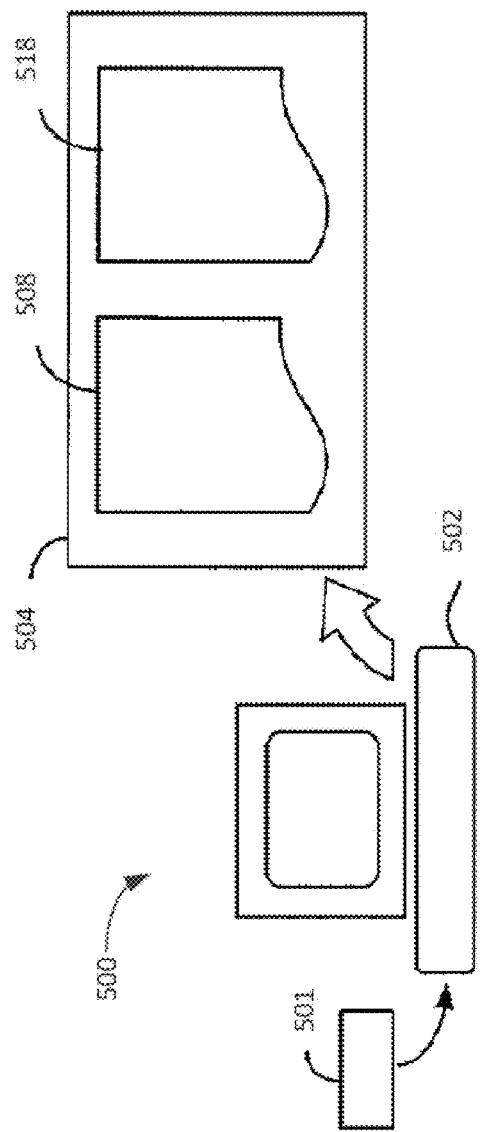
FIG. 7 is a block diagram that illustrates aspects of a bench-top system that can be used to obtain the measurements required to calculated the preclinical metrics that can provide as estimate of the clinical performance of the IOLs when implanted in a patient's eye.

FIG. 7 shows an implementation of a system that can be used to obtain metrics that characterize the clinical performance of the IOL designs. The system 500 includes one or more apparatuses capable of performing the measurements, calculations, assessments and comparisons of the metrics, as well as the determination of the corresponding simulated VA or simulated AU Defocus curve, according to the correlations described at the previous section. The system 500 can include processing electronics 502, and a computer readable memory or medium 504 coupled to the processing electronics 502. The computer readable memory 504 includes therein an array of ordered values 508 and sequences of instructions 518 which, when executed by the processing electronics 502, cause the processing electronics 502 to compute the metrics discussed above. The system 500 can be an optical bench and the corresponding computer required to analyze, record and process the raw data measured with such an optical bench.

The array of ordered values 508 can measure and/or record and/or include data related to one or more types of available IOL, models of optotypes, one or more models of the eye, etc. In some embodiments, the sequence of instructions 518 can include algorithms to measure the corresponding preclinical data to calculate the metrics for different defocus ranges and analyze the optical performance of the IOLs and relate that to their clinical performance.

The algorithms and/or formulae to calculate the metrics can be implemented as a set of instructions which are stored in a non-transitory computer medium and executed by processing electronics 502. The calculation of the metrics can be performed over the internet. The algorithms and/or formulae to calculate the metrics can be implemented as a mobile application which can be downloaded on a mobile device. The algorithms and/or formulae to calculate the metrics can be implemented as a software program that is a part of an instrument. An instrument to implement the methods described herein can comprise a set of apparatuses, including a set of apparatuses from different manufacturers that are configured to perform the necessary measurements and calculations. Any instrument comprising all needed measurements (MTF, PTF and/or recording the image yielded by the optical system with or without containing the IOL) as well as the needed calculations to implement the methods described herein can be considered as an inventive embodiment. The processing electronics may be embodied in a distributed computing system, general purpose desktop, laptop, tablet or mobile computer, and/or may comprise hardware and/or software.

The processing electronics 502 may be embodied in a general purpose desktop, laptop, tablet or mobile computer. In certain embodiments, the system 500 may be configured to be electronically coupled to another device, such as one or more instruments for obtaining measurements of the optical quality provided by each IOL in a particular physical eye model. Alternatively, the system 500 may be adapted to be electronically and/or wirelessly coupled to one or more other devices.

The system can be implemented as a bench-top optical system. In such implementations, the processing electronics 502 can be connected to an optical bench-top system 501 including an illumination source, an imaging system and one or more targets. Alternately, the system can be implemented on one or more computing devices using models for the target, the various implementations of the IOLs, white light source and the imaging system. In various implementations, the target can be an optotype including a plurality of characters and/or letters. For example, the metrics can be obtained from the evaluation of the images and/or MTF and/or PTF measurements yielded by different IOL designs. In various implementations, the target can include a plurality of objects with a wide range of spatial frequency content (e.g. between about 0 cycles per mm and about 200 cycles per mm). In various implementations, the target can be a 1951 USAF picture chart. In an alternative embodiment, the target can be a slit, oriented in any direction. The analysis of the image provided by the IOL under study once implanted in the particular eye model, allows for calculating the corresponding MTF and PTF at different spatial frequencies.

To obtain the MTFa, wMTF, wOTF and X-cor metrics, the through focus MTF and PTF (both for different spatial frequencies) and USAF pictures can be measured in an optical bench. As a way of example, these measurements can be performed at 3 mm pupil in white light. The optical conditions at which these measurements can be performed may depend on the optical conditions for which the correlation with clinical data as described in the previous sections has been developed. Alternatively, optical bench measurements can be performed in any combination of light conditions and pupil size that fulfill the previous requirement. Without any loss of generality, the pupil sizes referred to herein can represent the exposed central area of the IOL under test, which can differ from the aperture stop of the test system.

To obtain the AU MTFa, AU wMTF, AU wOTF and AU X-cor metrics, the through focus MTF and PTF (both for different spatial frequencies) and USAF pictures can be measured in an optical bench. As a way of example, these measurements can be performed at 3 mm pupil in white light. The optical conditions at which these measurements can be performed may depend on the optical conditions for which the correlation with clinical data as described in the previous sections has been developed. Alternatively, optical bench measurements can be performed in any combination of light conditions and pupil size that fulfill the previous requirement. Without any loss of generality, the pupil sizes referred to herein can represent the exposed central area of the IOL under test, which can differ from the aperture stop of the test system.

The imaging system can be configured to be in communication with processing electronics (e.g., processing electronics 502) that are configured to calculate the area under the MTF (MTFa) curve for a range of spatial frequencies (e.g. between 0 cycles per mm to 50 cycles per mm) for each defocus position (e.g. from −3 D to 0 D in steps of 0.5 D) from the measured through focus MTF and/or PTF obtained for several different spatial frequencies, and/or USAF pictures. Alternatively, the system can be configured to obtained the wMTF and wOTF for a range of spatial frequencies (e.g. between 0 cycles per mm and the maximum spatial frequency measured or between 0 cycles per mm and 150 cycles per mm) for each defocus position (e.g. from about −3.0 D to about 0 D in steps of 0.5 D). The processing electronics can be further configured to calculate the X-cor for each defocus position (e.g., between about −3.0 D and about 0 D in steps of 0.5 D). Furthermore, the simulated VA can be calculated for each of these metrics making use of the regressions shown in the previous section.

As a way of example, FIG. 8A shows a comparison between the simulated VA calculated for a first model and the clinical VA measured in patients bilaterally implanted with the first IOL model. FIG. 8B shows a comparison between the simulated VA calculated for a second model and the clinical VA measured in patients bilaterally implanted with the second IOL model. FIGS. 8A and 8B show the simulated VA calculated for a range of defocus positions between about 0 D and about −3.0 D for each particular metric making use of the correlations shown in FIGS. 1A-1D. For example, in FIG. 8A, curve 610a refers to the preclinical metric wOTF for the first IOL model, curve 612a refers to the preclinical metric wMTF for the first IOL model, curve 614a refers to the preclinical metric X-cor for the first IOL model and curve 616a refers to the preclinical metric MTFa for the first IOL model integrated for spatial frequencies between 0 cpmm and 50 cpmm. Referring to FIG. 8B, curve 610b refers to the preclinical metric wOTF for the second IOL model, curve 612b refers to the preclinical metric wMTF for the second IOL model, curve 614b refers to the preclinical metric X-cor for the second IOL model and curve 616b refers to the preclinical metric MTFa for the second IOL model integrated for spatial frequencies between 0 cpmm and 50 cpmm. The clinical results provided by both IOLs are also included in FIGS. 8A and 8B. Curve 605a represents the clinical VA for different defocus positions between 0 D and −3.0 D measured in patients implanted with the first IOL model. Curve 605b represents the clinical VA for different defocus positions between 0 D and −3.0 D measured in patients implanted with the second IOL model.

FIG. 9A shows the absolute difference between the simulated VA calculated for a first IOL model and the clinical VA measured in patients bilaterally implanted with the first IOL model for different defocus positions between about 0 D and about −3.0 D. FIG. 9B shows the absolute difference between the simulated VA calculated for a second IOL model and the clinical VA measured in patients bilaterally implanted with the second IOL model for different defocus positions between about 0 D and about −3.0 D. Referring to FIG. 9A, bar 705a represents the pre-clinical metric MTFa integrated for spatial frequencies between 0 cpmm and 50 cpmm, bar 709a represents the pre-clinical metric wMTF, bar 711a represents the pre-clinical metric wOTF and bar 713a represents the pre-clinical metric X-cor. Referring to FIG. 9B, bar 705b represents the pre-clinical metric MTFa integrated for spatial frequencies between 0 cpmm and 50 cpmm, bar 709b represents the pre-clinical metric wMTF, bar 711b represents the pre-clinical metric wOTF and bar 713b represents the pre-clinical metric X-cor.

It is noted that the absolute difference between the simulated VA calculated for an IOL model and the clinical VA measured in patients bilaterally implanted with the same IOL model for different defocus positions between about 0 D and about −3.0 D is lower than 0.1 Log MAR for most of the defocus positions and most of the preclinical metrics. Therefore, any of the metrics can be used to predict the VA measured in patients implanted with these IOLs for which the preclinical metrics have been calculated. Furthermore, the preclinical metrics described above can be used to develop newer correlations when clinical and preclinical data for the other IOL models are available. Alternatively, these preclinical metrics, together with existing correlations to clinical data for other IOL models, can be used to predict the though focus simulated VA for new IOL models or prototypes. In another embodiment, existing correlation to clinical data can serve to determine preclinical levels related to clinical effectiveness and safety requirements.

The MD parameter described above can be also calculated to assess the degree of monotonic decrease that simulated VA shows from distance vision. FIG. 10A shows the simulated VA calculated with preclinical metrics MTFa represented by curve 809a and wOTF represented by curve 813a for different defocus positions between about 0 and −3.0 D for a first IOL model. FIG. 10A also shows the clinical VA represented by curve 805a for different defocus positions between about 0 and −3.0 D measured in patients implanted with the first IOL model. The data points for the simulated preclinical metric MTFa are fit with a linear function represented by curve 807a and the data points for the simulated preclinical metric wOTF are fit with a linear function represented by curve 811a.

FIG. 10B shows the simulated VA calculated with preclinical metrics MTFa and wOTF represented by curve 813b for different defocus positions between about 0 and −3.0 D for a second IOL model. FIG. 10B also shows the clinical VA represented by curve 805b for different defocus positions between about 0 and −3.0 D measured in patients implanted with the second IOL model. The data points for the simulated preclinical metric MTFa are fit with a linear function represented by curve 807b and the data points for the simulated preclinical metric wOTF are fit with a linear function represented by curve 811b.

From the slope and correlation coefficient of the linear fit curves, the MD parameter was calculated. Table 4 below shows the corresponding slope, correlation coefficient and resulting MD parameter for the first IOL model (IOL1) and the second IOL model (IOL2). Both the slope (in absolute value) and the correlation coefficient are greater for IOL1 than for IOL2, resulting in a smaller MD parameter for IOL1 than for IOL2. This indicates that simulated VA decreases monotonically from the distance peak for IOL1 than for IOL2. Furthermore, and due to the fact that the slope for IOL1 is greater in absolute value than for IOL2, the decrease in VA is greater for IOL1 than for IOL2, indicating that IOL2 provides a better estimate of VA at intermediate and near vision distances than IOL1. Therefore, the MD parameter can be used to rank the degree of monotonic decrease and the near and/or intermediate performance of existing or new IOLs prototypes.

TABLE 4

The slope, correlation coefficient and MD parameter calculated
from the linear fitting of the simulated VA for two IOL models

| | MTFa | | | wOTF | | |
|---|---|---|---|---|---|---|
| | Slope | R2 | MD Parameter | Slope | R2 | MD Parameter |
| IOL1 | −0.248 | 0.99 | −0.25 | −0.243 | 0.99 | −0.24 |
| IOL2 | −0.003 | 0.001 | −3.2E−6 | −0.027 | 0.13 | −0.004 |

The area under (AU) each particular metric integrated for different defocus positions between about −0.5 D and about −2.0 D and the AU X-cor over the defocus range (e.g. between −2 D to −0.5 D) were calculated for each IOL design. Simulated AU Defocus curve can be calculated along with the correlations described in the previous section. FIG. 11 shows the simulated AU Defocus curve calculated from each particular preclinical metric for IOL1 and a multifocal IOL with an add power of +2.75 D (IOL3), as compared to the AU Defocus curve measured in patients implanted with the same IOLs. These defocus curves were measured in patients bilaterally implanted with the same IOL. The defocus curves were obtained by measuring high contrast through focus VA using the ETDRS chart with best distance correction in place. AU Defocus calculated from all preclinical metrics showed a good correspondence with the clinical values. The simulated AU defocus curve for IOL1 is lower than that for IOL3, indicating the IOL3 provides with intermediate performance in terms of visual acuity than IOL1. Therefore, the AU Defocus curve calculated from preclinical metrics is a powerful method to rank the visual performance provided at intermediate distances by different IOL designs.

FIG. 12A shows a comparison between the simulated CS at 6 cpd at distance calculated for a two IOL models (IOL1 and IOL2) from the different preclinical metrics MTFa, wMTF, wOTF and X-cor and the clinical CS at 6 cpd measured in patients bilaterally implanted with the same IOL models. FIG. 12B shows a comparison between the simulated CS at 12 cpd at distance calculated for two IOL models (IOL1 and IOL2) from the different preclinical metrics MTFa, wMTF, wOTF and X-cor and the clinical CS at 12 cpd measured in patients bilaterally implanted with the same IOL models. FIGS. 12A and 12B show the simulated CS at 6 and 12 cpd respectively calculated at distance for each particular metric making use of the correlations shown in FIGS. 5A-6D. The good agreement between simulated and measured values at both spatial frequencies shows the predictive value of the preclinical metrics also for contrast sensitivity. Although the comparison between simulated and measured values is made herein only for distance, these metrics can also be used to predict and assess the clinical through focus and/or intermediate and/or near contrast sensitivity from preclinical data.

Different metrics can be used to evaluate the optical performance of rotationally asymmetric IOLs at intermediate distances. For example, radially averaged MTF (rMTF) can be used instead of MTF to calculate the MTFa. In various implementations, rMTF can be measured for different orientations and averaged. The MTFa can then be calculated by calculating the area under the rMTF for a range of spatial frequencies.

The metrics herein described can be calculated from measured values in in-vitro conditions. In an alternative embodiment, these preclinical metrics and the corresponding correlations with clinical data can be calculated from wavefront aberrations measurements. In an alternative embodiment, these preclinical metrics and the corresponding correlations with clinical data can be calculated from ray tracing simulations. These calculations can retrieve the simulated MTF, PTF and/or simulated USAF pictures, from which the different metrics discussed above can be calculated. These calculations can be used to develop new correlations with clinical results for these IOL models for which these are available. Alternatively, they can be used to assess the intermediate performance or to simulate the clinical VA or the degree of monotonic decrease or tolerance to refractive errors for new IOL models. These correlations can be used to assess the clinical contrast sensitivity at 6 and 12 cpd at distance and/or intermediate and/or near. These simulations can be performed in physical or realistic eye models.

The metrics described herein can be used to develop new correlations with the clinical performance of the IOL models (e.g. driving simulation). The preclinical measurements described herein can be fitted to clinical data or to data obtained from adaptive optics visual simulation. It has been shown that visual acuity and contrast sensitivity measured when inducing the phase profile corresponding to different IOL models using adaptive optics corresponds to visual performance measured in patients implanted with the same IOLs (Schwarz et al ARVO 2014 and Manzanera et al ARVO 2015). Therefore, both, the data obtained in clinical studies involving patients implanted with IOLs and data measured using adaptive optics visual simulation can be used to fit the preclinical information measured in optical bench testing to get the above described preclinical metrics.

The metrics described herein can be calculated for different pupil sizes. The pupil size can be adapted to the light conditions. For example, 4.5 mm pupil size can be used to simulate mesopic conditions in pseudophakic patients.

The metrics described herein can be calculated for different ranges of defocus position. For example, they can be calculated between about −2.0 D and −0.5 D to evaluate intermediate vision, between about −3.5 D and −2.0 D to evaluate near vision or between about −0.5 D and −0 D to evaluate far vision or between +0.5 D and −0.5 D to evaluate tolerance to refractive errors The metrics described herein can be calculated for different ranges of defocus position. For example, they can be calculated between about −2.0 D and −0.5 D to evaluate intermediate vision, between about −3.5 D and −2.0 D to evaluate near vision or between about −0.5 D and −0 D to evaluate far vision or between +0.5 D and −0.5 D to evaluate tolerance to refractive errors Although, the above disclosure is related to using metrics to evaluate the clinical performance of intraocular lenses (IOLs), the metrics can be used to evaluate the clinical performance of contact lenses, refractive surgery and/or spectacle lenses.

The above presents a description of the best mode contemplated of carrying out the embodiments described herein, and of the manner and process of making and using it, in such full, clear, concise, and exact terms as to enable any person skilled in the art to which it pertains to make and use of the embodiments described herein. The embodiments described herein can be modified and alternate constructions from that discussed above which are fully equivalent. Consequently, it is not the intention to limit the disclosure to the particular embodiments disclosed. On the contrary, the intention is to cover modifications and alternate constructions coming within the spirit and scope of the invention as generally expressed by the following claims, which particularly point out and distinctly claim the subject matter of the invention.

We claim:

1. An optical system configured to predict clinical visual performance of an intraocular lens (IOL), the system comprising:
an IOL optical quality measurement device configured to acquire a plurality of images of a target including objects with different spatial frequencies and obtain modulation transfer function (MTF) and/or phase transfer function (PTF) at different spatial frequencies for different defocus positions of the IOL in a vision range from the acquired plurality of images, the measurement device comprising:
a processor configured to execute programmable instructions stored in a non-transitory computer storage medium to calculate a metric based on at least one preclinical metric selected from:
an area under the MTF (MTFa) obtained by integrating preclinical through focus MTF measurements obtained for different spatial frequencies between 0 cycles per mm and 200 cycles per mm for each of the different defocus positions;
a cross correlation coefficient (X-cor) corresponding to a convolution of a reference image and the plurality of images acquired by the IOL optical quality measurement device at each of the different defocus positions;
a weighted MTF (wMTF) obtained by integrating a product of a threshold contrast sensitivity ($CS_{th}$) and through focus MTF measurements obtained for different spatial frequencies between 0 cycles per mm and 200 cycles per mm for each of the different defocus positions; or
a weighted OTF (wOTF) obtained by integrating a product of a threshold contrast sensitivity ($CS_{th}$), through focus MTF measurements, and cosine of the PTF obtained for different spatial frequencies between 0 cycles per mm and 200 cycles per mm for each of the different defocus positions; and
obtain a correlation between the calculated metric and clinical data that predicts visual acuity (VA) at different defocus positions of the intraocular lens (IOL).

2. The system of claim 1, wherein the measurement device comprises:
a reference image illuminated by a light source; and
an imaging system including a pupil.

3. The system of claim 2, wherein the light source is a white light source.

4. The system of claim 2, wherein the pupil has a size between 1 mm and 6 mm.

5. The system of claim 1, wherein the objects have spatial frequencies between about 0 cycles per mm (cpmm) and 200 cpmm.

6. The system of claim 1, wherein the target is selected from the group consisting of an optotype, a slit, a 1951 USAF picture chart; and a subset of bars from a 1951 USAF picture chart.

7. The system of claim 1, wherein the measurement device is a computing device including the processor, the computing device configured to simulate the plurality of images using models for the target and the IOL.

8. The system of claim 1, wherein the metric is based on at least two preclinical metrics selected from:
the area under the MIT (MTFa) for each of the different defocus positions;
the cross correlation coefficient (X-cor) for the acquired plurality of images at each of the different defocus positions;
the weighted MIT (wMTF) for each of the different defocus positions; or
the weighted OTF (wOTF) for each of the different defocus positions.

9. The system of claim 1, wherein the different defocus positions are between 0 D and −3.0 D.

10. The system of claim 1, wherein the processor is configured to calculate the area under the MTF (MTFa) according to $$\sum_{f=1}^{50} \frac{d}{50} MTF(fd),$$

wherein f denotes a spatial frequency in cycles per mm, and d denotes sampling size for preclinical measurement of MTF at each spatial frequency f.

11. The system of claim 1, wherein the processor is configured to calculate the weighted MTF (wMTF) according to $$\sum_{f=1}^{150} \frac{d}{50} MTF(fd)CS_{th}(fd),$$

wherein f denotes a spatial frequency in cycles per mm, and d denotes sampling size for preclinical measurement of MTF at each spatial frequency f.

12. The system of claim 1, wherein the processor is configured to calculate the weighted OTF (wOTF) according to $$\sum_{f=1}^{150} \frac{d}{50} MTF(fd)CS_{th}(fd)\cos(PTF(fd)),$$

wherein f denotes a spatial frequency in cycles per mm, and d denotes sampling size for preclinical measurement of MTF at each spatial frequency f.

* * * * *